United States Patent [19]

Stead et al.

[11] Patent Number: 4,851,528

[45] Date of Patent: Jul. 25, 1989

[54] ANTHRAQUINONE DERIVATIVES

[75] Inventors: Cecil V. Stead, Blackley; Steven J. Burton, Chorley; Christopher R. Lowe, Saffron Walden, all of England

[73] Assignee: Imperial Chemical Industries PLC, London, England

[21] Appl. No.: 900,695

[22] Filed: Aug. 27, 1986

[30] Foreign Application Priority Data

Aug. 27, 1985 [GB] United Kingdom ................ 8521328

[51] Int. Cl.$^4$ ................ C07D 251/00; C07C 143/665
[52] U.S. Cl. ..................................... 544/189; 260/372
[58] Field of Search ............... 260/374, 377, 372; 544/189, 187

[56] References Cited

U.S. PATENT DOCUMENTS

| | | | |
|---|---|---|---|
| 2,773,871 | 12/1956 | Brassel et al. | 260/374 |
| 2,889,323 | 6/1959 | Heslop | 260/374 |
| 3,433,810 | 3/1969 | Rickenbacher | 260/377 |
| 3,823,167 | 7/1974 | Peters et al. | 260/372 |
| 4,198,205 | 4/1980 | Elser et al. | 544/189 |
| 4,276,047 | 6/1981 | Imahori et al. | 544/189 |

OTHER PUBLICATIONS

Abrahart, *Dyes and Their Intermediates*, 1968, pp. 8–9.

*Primary Examiner*—Richard L. Raymond
*Assistant Examiner*—Raymond Covington
*Attorney, Agent, or Firm*—Cushman, Darby & Cushman

[57] ABSTRACT

A water-soluble anthraquinone compound of the formula:

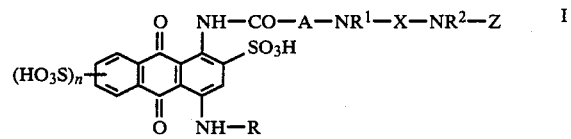

wherein
A represents a divalent hydrocarbon group;
X represents a divalent hydrocarbon group; and
$R^1$ & $R^2$ each independently is H or alkyl or together, with X and the N atoms to which they are attached, represent a diazaheterocycle;
R represents a monovalent hydrocarbon group;
n is 0 or 1;
Z is H or a group, Y—B;
Y is a divalent heterocycle; and
B is an activated halogen atom, and an adduct thereof with a carbohydrate substrate, capable of selectively absorbing certain proteinaceous materials and suitable for use in the chromatographic separation of proteins.

6 Claims, No Drawings

ANTHRAQUINONE DERIVATIVES

This specification describes an invention relating to an anthraquinone (AQ) derivative and to protein adsorbents and precipitants prepared from the anthraquinone derivative which are of value in the separation and purification of proteins.

Cellulose-reactive dyes are well established products which are widely used in the textile industry for the coloration of cotton, viscose and other cellulosic textiles. The molecule of such a reactive dye may be viewed as being made up of two interlinked units, each of which has a different function. One unit is the chromophore whose function is to impart the desired colour and other tinctorial properties to the textile. The other unit is the fibre reactive group which, under well established application conditions, reacts chemically with cellulose to covalently bind the dye molecules to the textile to produce a dyed material which is highly resistant to washing processes.

Whilst cellulose-reactive dyes were initially developed to solve certain problems encountered in the dyeing and printing of cellulosic textile materials, they have, or over the years, been found to possess properties, which make them of use outside the textile dyeing field.

It is known, for example from U.S. Pat. No. 4,016,149 and WO 7900541, that these dyes can be attached by similar techniques to carbohydrate substrates, such as polymers and co-polymers derived from agarose, dextrose, dextrans, etc. Adducts of such carbohydrate substrates and certain commercially available reactive dyes have been used as adsorbents for the chromatographic separation of certain proteinaceous materials. Amongst the commercial textile dyes which have been used in this manner for protein separation are certain simple blue AQ dyes, such as CI Reactive Blue 2, which has the following formula:

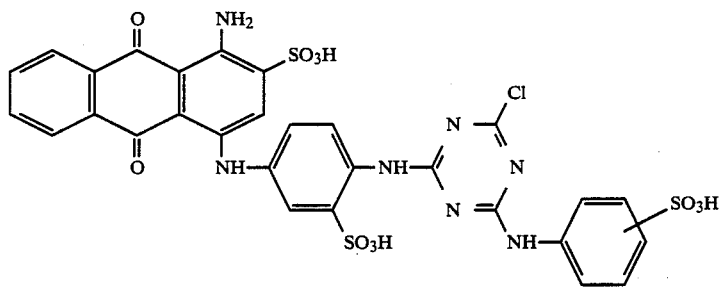

Many dyes of this type are found in the ranges of reactive dyes from various dye manufacturers. The molecular characteristic of this class of cellulose reactive dye is that the members are salts, usually sodium salts, of 1-amino-4-arylamino-AQ-2-sulphonic acids, in which the aryl unit is generally a single benzene ring further substituted with a sulphonic acid group and a halogeno-heterocyclic fibre reactive group attached to the benzene ring through an imino group. The monochlorotriazine reactive group present in the dye of Formula (A), may be replaced by a different cellulose-reactive halogenoheterocyclic group, such as dichloropyrimidinyl, difluoropyrimidinyl, trichloropyrimidinyl, 5-chlorodifluoropyrimidinyl, 5-cyanodichloropyrimidinyl or dichlorotriazinyl, but the preferred reactive group is monochlorotriazinyl.

It is also known that suitable compounds containing a free amino group can be attached to a hydroxyl group of a carbohydrate substrate through a carbonyl bridge group, by sequential reaction of the carbohydrate substrate with a reactive carbonyl compound such as carbonyl-di-imidazole. In this way it is possible to attach the precursor of such a cellulose reactive dye, containing a free amino group, to the carbohydrate subsrate to form a protein absorbent.

According to a first aspect of the present invention there is provided a water-soluble anthraquinone compound of the formula:

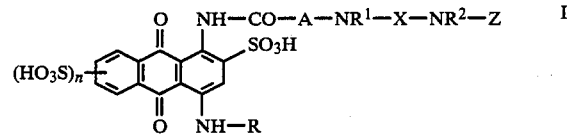

wherein

A represents a divalent hydrocarbon group;
X represents a divalent hydrocarbon group; and
$R^1$ & $R^2$ each independently is H or alkyl or together, with X and the N atoms to which they are attached, represent a diazaheterocycle;
R represents a monovalent hydrocarbon group;
n is 0 or 1; and
Z is H or a group, $-Y-B$;
Y is a divalent heterocycle; and
B is an activated halogen atom.

The divalent group, A, is preferably an alkylene group, especially one containing up to 6 carbon atoms, and may carry one or more substituents, e.g. hydroxy and halogen, but is preferably unsubstituted. It is especially preferred that A is a group of the formula, $-(CHR^3)_m-$, in which $R^3$ is H or $C_{1-4}$-alkyl and $m=1$ or 2, but preferably 1. It is further preferred that $R^3$ is H, especially when $m=2$. Examples of A are ethylene, ethylmethylene, methylethylene and especially methylene.

The divalent group, X is conveniently alkylene or arylene, especially $C_{2-6}$-alkylene or phenylene, each of which may carry substituents, e.g. hydroxy, halogen, sulphonate and carboxylate, but is preferably unsubstituted. Examples of X are ethylene, propylene, hexamethylene and phen-1,4-ylene.

The groups, $R^1$, $R^2$ & $R^3$ are preferably H or $C_{1-4}$-alkyl which may carry substituents, such as hydroxy or halogen, but are more preferably unsubstituted. Where $R^1$ & $R^2$ are linked to form, with X and the N atoms, a heterocycle, this is preferably a piperazin-1,4-ylene group.

The monovalent group, R, may be alkyl, aryl or aralkyl, especially $C_{1-4}$-alkyl, phenyl and benzyl, which may carry substituents, such as hydroxy, halogen, sulphonate and carboxylate.

It is preferred that the group R is an aryl group which may carry substituents such as $C_{1-4}$-alkyl; $C_{1-4}$-alkoxy; acylamino, preferably acetylamino; and more especially sulphonic acid or carboxylic acid groups.

Examples of groups represented by R are methyl, butyl, benzyl, phenyl, 3'- and 4'-sulphophenyl, 4'-acetylamino-3'-sulphophenyl, 2'-methyl-5'-sulphophenyl, 2'-methoxy-5'-sulphophenyl and 3'- and 4'-carboxyphenyl. Especially valuable groups represented by R conform to the formula:

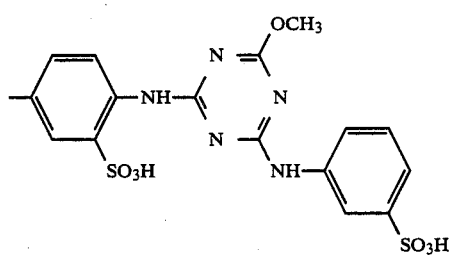
II wherein W represents aryl, especially phenyl, preferably carrying sulphonic or carboxylic acid groups and V represents an $C_{1-4}$-alkoxy, amino, $C_{1-4}$-alkylamino or di($C_{1-4}$-alkyl)amino group. Examples of preferred groups represented by W are 2-sulphophenyl, 3-sulphophenyl and 3-carboxyphenyl. A preferred substituent of Formula II is:

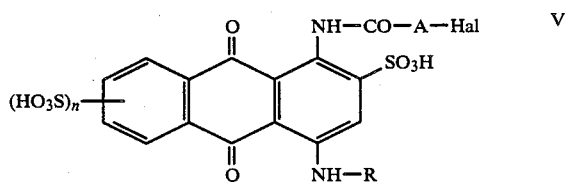
III

The group, —Y—B, preferably comprises an activated halogen atom, B, attached to a divalent heterocycle, Y, for example a heterocyclic cellulose-reactive group, such as dichloropyrimidinyl, difluoropyrimidinyl, trichloropyrimidinyl, 5-chlorodifluoropyrimidinyl, 5-cyanodichloropyrimidinyl, dichlorotriazinyl or, more preferably, monochlorotriazinyl, In the preferred group Y—B, B is chlorine and there is only one activated halogen atom. Where the cellulose-reactive reactive group, —Y—B, contains a single reactive halogen atom but is derived from a polyhalo-heterocycle, such as cyanuric chloride, the excess halogen atoms are preferably replaced by monovalent groups, especially a mono- or bicyclic aryl group, such as phenyl or naphthyl ether, of which may be substituted. Suitable substituents or sulphonate, carboxylate, nitro, $C_{1-4}$-alkyl or alkoxy and halogen, such as chlorine and bromine. Examples of preferred monovalent groups attached to the haloheterocycle are 2,5-disulphoanilino, 3-sulphoanilino and 4-sulphoanilino.

The compound of Formula I in which R is —Y—B may be attached to a carbohydrate substrate through reaction of the activated halogen atom with hydroxy groups in the carbohydrate. The compound of Formula I in which R is H may be attached to a carbohydrate substrate through activation of the substrate with carbonyl-di-imidazole followed by reaction of the activated substrate with the compound of Formula I. In both cases there is formed a material useful as an protein absorbent in the chromatographic separation of proteins.

According to a second feature of the present invention there is provided a compound of the formula:

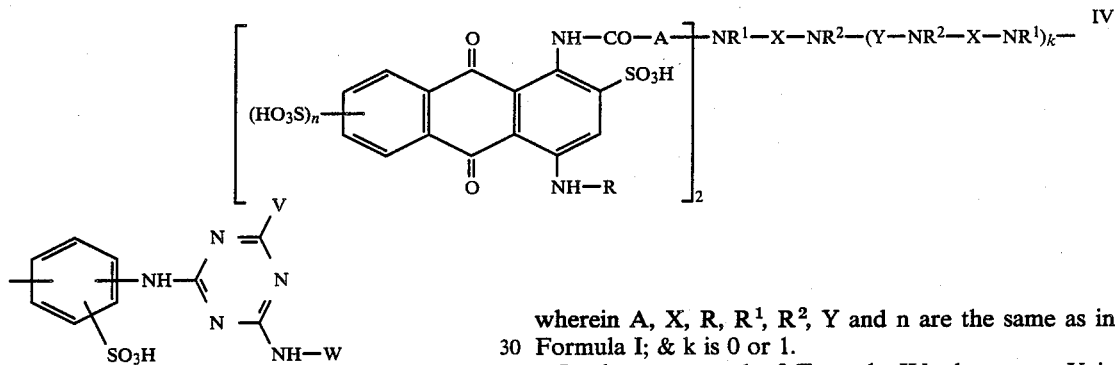
IV wherein A, X, R, $R^1$, $R^2$, Y and n are the same as in Formula I; & k is 0 or 1.

In the compound of Formula IV, the group Y is preferably free from activated halogen atoms and, where Y is derived from a polyhalo-heterocycle containing more than two activated halogen atoms, the excess halogen atoms are preferably replaced by other inactive groups as hereinbefore described.

The compound of Formula IV containing two anthraquinone moieties is useful as protein precipitant and acts as a protein precipitant, linking protein molecules together until an insoluble structure is obtained.

The compounds of Formula I & Formula IV preferably contain sufficient water-solubilising groups, such as sulphonate and/or carboxylate groups, to render them water-soluble to at least 5% by weight. Such groups may be present in the anthraquinone nucleus or in the substituent groups, as hereinbefore described.

The compound of Formula I wherein Z is —Y—B may be prepared by reaction of an anthraquinone compound of Formula I wherein Z is H with a polyhalogenoheterocyclic compound having at least two activated halogen atoms under condition such that at least one activated halogen atom remains unreacted.

The compound of Formula I wherein Z is H may be prepared by reaction of a compound of the formula:

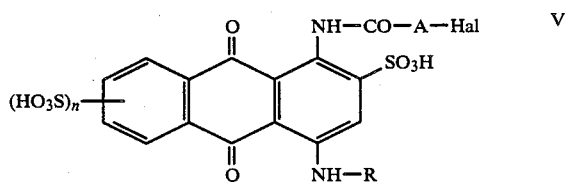
V wherein A, R, and n are as hereinbefore defined and Hal is a halogen atom, with a diamine, $R^1NH—X—NHR^2$ wherein X, $R^1$ and $R^2$ are as hereinbefore defined.

The compound of Formula V may be prepared by reaction of a compound of the formula:

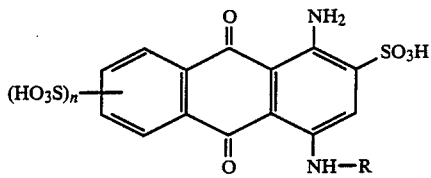

wherein R and n are as hereinbefore defined, with a halogenacyl halide Hal—CO—A—Hal, wherein A and Hal are as hereinbefore, defined.

The compound of Formula IV may be prepared in an analogous manner by reacting a compound of Formula V with a compound of Formula I in which Z is H or by reacting a compound of Formula I in which Z is H with a compound of Formula I in which Z is —Y—B.

According to a third aspect of the present invention there is provided a protein adsorbent comprising the adduct of at least one compound of Formula I in which Z is —Y—B and a substrate having at least one group capable of reaction with the reactive halogen atom, B, in said compound. According to a fourth aspect of the present invention there is provided a protein adsorbent comprising the adduct of at least one molecule of a compound of Formula I in which Z is H and a substrate having at least one hydroxy group linked together through a carbonyl group between the nitrogen atom to which Z is attached and the oxygen atom of the hydroxy group. The substrate may be a substantially water-insoluble, solid support or a water-soluble polymer. As examples of the solid support there may be mentioned acrylic polymers and co-polymers, silica, titania, alumina, hydroxyalkylmethacrylates, porous glass, but the preferred water-insoluble solid support is a polymeric substrate having a plurality of hydroxyl groups to which the compound of Formula I may become attached through the cellulose reactive group or a carbonyl bridge as hereinbefore described. Especially suitable substrates are carbohydrates and modified carbohydrates. Examples of a suitable carbohydrate substrate are agarose, cross-linked agarose, dextrose, dextrans, and modified versions thereof, such as are available as "Sepharose" and "Sephadex" gels ("Sepharose" and Sephadex" are trade marks of Pharmacia Fine Chemicals) and are described in GB 1540165 (Cutter). Other polymeric substrates are polyamides and polyacrylamides. Especially preferred substrates are agarose and cross-linked agarose.

The adsorbent comprising a dye bound to a solid support may be in the form of a column for chromatographic separation purposes or in the form of a membrane to allow separation to be carried out in a membrane separation format.

As examples of water-soluble polymers which may be reacted with dyes of Formula I there may be mentioned dextran or polyethylene glycols, the products of the reaction being used to separate protein materials in an aqueous two-phase partition process.

The adsorbents disclosed in accordance with the third aspect of the present invention may be prepared in standard techniques, for example, by reacting a compound of Formula I in which Z is —Y—B with the carbohydrate substrate in the presence of an acid binding agent, such as an alkali metal hydroxide or carbonate, e.g. NaOH or Na$_2$CO$_3$ or by reacting the carbohydrate substrate with carbonyl di-imidazole and subsequently with a compound of Formula I in which Z is H. Methods for the preparation of such absorbents and chromatographic columns containing them are well documented, see for example WO 7900541 and US 4016149.

The adsorbents and the precipitants of Formula II have greatly enhanced binding efficiency for certain biological molecules such as proteins and enzymes, especially enzymes such as nicotinamide nucleotide-dependent oxido-reductases; phosphokinases; coenzyme-A dependent enzymes; hydrolases; acetyl-, phosphoriboxyl- and aminotransferases; RNA and DNA nucleases and polymerases; restriction endonucleases; synthetases; hydroxylases; and a number of proteins such as serum albumin; clotting and complement factors; phytochrome; lipoproteins; and interferon, and are especially well adapted for the separation of such species from mixtures of proteins.

Examples of the enzymes and proteins to which the adsorbents and precipitants of the present invention are especially adapted for binding are alcohol dehydrogenase (horse liver), lactase dehydrogenase (rabbit muscle), serum albumin (human blood), and chymotrypsin (bovine pancreas).

The present invention is further illustrated by the following examples in which all parts and percentages are by weight unless otherwise indicated.

EXAMPLE 1

A solution of 7.4 parts of 2-methoxy-4,6-dichloro-s-triazine in 50 parts of acetone was poured into 200 parts of water and the stirred suspension warmed to 25° C. and a solution of 21.3 parts of the disodium salt of 1-amino-4-(3-sulpho-4-aminoanilino)anthraquinone-2-sulphonic acid in 400 parts of water added, the pH being maintained at between 6 and 7 during the addition and for three hours afterwards by the addition of a molar solution of sodium hydroxide as required. A solution of 23.4 parts of the sodium salt of orthanilic acid in 500 parts of water was then added and the mixture stirred at between 90° and 95° C. during 32 hours whilst the pH was maintained at between 6 and 7 by the addition of a molar solution of sodium hydroxide. 160 Parts of sodium chloride were then added and the precipitated trisodium salt of 1-amino-4-(4-[2-methoxy-4-(2-sulphoanilino)-s-triazin-6-yl]-amino-3-sulphoanilino)anthraquinone-2-sulphonic acid filtered off from the cooled mixture, washed with 500 parts of a 20% solution of sodium chloride in water and dried at 50° C.

31.9 Parts of chloroacetyl chloride were added over 10 minutes to a stirred solution of 20.8 parts of the trisodium salt of 1-amino-4-(4-[2-methoxy-4-(2-sulphoanilino)-s-triazin-6-yl]amino-3-sulphonanilino)-anthraquinone-2-sulphonic acid in 150 parts of dimethylformamide and the mixture stirred for a further 30 minutes and then added to a 800 parts of a saturated aqueous solution of sodium chloride. The precipitated trisodium salt of 1-chloroacetylamino-4-(4-[2-methoxy-4-(2-sulphoanilino)-s-triazin-6-yl]amino-3-sulphoanilino)-anthraquinone-2-sulphonic acid was filtered off, washed with 300 parts of a 15% aqueous solution of sodium chloride and dried in vacuo. The dried powder was added to a solution of 9 parts of ethylene diamine in 75 parts of dimethylformamide and the mixture stirred for 25 minutes at 25° C. 800 Parts of a saturated aqueous solution of sodium chloride were then added and the precipitated trisodium salt of 1-beta-aminoethylaminoacetylamino-4-(4-[2-methoxy-4-(2-sulphoanilino)-s-triazin-6-yl]-amino-3-sulphoanilino)anthraquinone-2-sulphonic acid filtered off, washed with 50 parts of a 10% aqueous solution of sodium chloride and dried in vacuo.

Further compounds in accordance with the invention were prepared by replacing the 23.4 parts of the sodium salt of orthanilic acid used in the above Example by the equivalent amount of the sodium salt of the amino acid shown in Column II of Table 1

TABLE 1

| I | II |
|---|---|
| Example 2 | sulphanilic acid |
| Example 3 | 3-aminobenzoic acid |

EXAMPLE 4

A solution of 9.35 parts of the trisodium salt of 1-(2-aminoethylaminoacetylamino)-4-(3-sulpho-4-[2-methoxy-4-(2-sulphoanilino)-s-triazin-6-ylamino]anilino)anthraquinone-2-sulphonic acid in 400 parts of water was added to a freshly prepared solution of 4.5 parts of the disodium salt of 1-(2,4-dichloro-s-triazin-6-ylamino)benzene-2,5-disulphonic acid in 100 parts of water and the mixture stirred for two hours at 35° C. whilst maintaining the pH at between 8 and 9. 80 Parts of sodium chloride were then added and the precipitated pentasodium salt of 1-(2-[2-chloro-4-(2,5-disulphoanilino)-s-triazin-6-ylamino]ethylaminoacetylamino)-4-(3-sulpho-4-[2-methoxy-4-(2-sulphoanilino)-s-triazin-6-ylamino]anilino)anthraquinone-2-sulphonic acid filtered off and dried in vacuo.

EXAMPLE 5

The trisodium salt of 1-(2-aminoethylaminoacetylamino)-3-sulpho-4-(4-[2-methoxy-4-(2-sulphoanilino)-s-triazin-6-ylamino]anilino)anthraquinone-2-sulphonic acid, prepared as described in Example 1, was immobilised on carbonyl di-imidazole activated Sepharose 4B in the usual manner. The dye concentration on the adsorbent was determined spectrophotometrically at 2.05 µM per g moist weight. A glass mino-column was packed with 1 g moist weight of the resultant adsorbent and equilibrated with 20 mM HEPES/NaOH pH7 buffer containing 1 mM reduced glutathione. Crude horse liver alcohol dehydrogenase was dialysed overnight at 4° C. against 150 volumes of HEPES/glutathione equilibration buffer and 2 ml, containing about 110 mg protein, permeated through the gel bed at a flow rate of 30 ml.hr$^{-1}$.cm$^{-2}$. The column was flushed with 10 ml of the equlibration buffer and adsorbed proteins eluted with 1M aqueous KCl. There was recovered 86% of the enzyme showing a 10.3 fold increase in purity.

In a similar way, chromatography of horse liver alcohol dehydrogenase over an adsorbent prepared using the compound of Example 2 gave a 36% recovery and a 3.1 fold increase in purity. Chromatography of horse liver alcohol dehydrogenase over an adsorbent prepared using the compound of Example 3 gave a 74% recovery and a 5.6 fold increase in purity.

We claim:

1. A water-soluble anthraquinone compound of the formula:

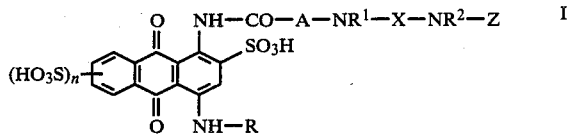

wherein
A represents a divalent hydrocarbon group;
X represents a divalent hydrocarbon group; and
$R^1$ & $R^2$ each independently is H or alkyl or together, with X and the N atoms to which they are attached, represent a diazaheterocycle;
R represents a monovalent hydrocarbon group;
n is 0 or 1;
Z is H or a group, $-Y-B$;
Y is a divalent heterocycle; and
B is an activated halogen atom.

2. A water-soluble anthraquinone compound of the formula:

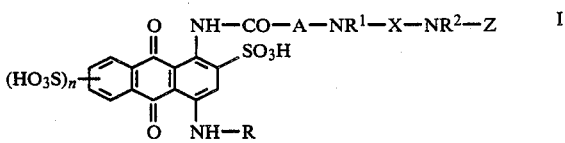

wherein
A is alkylene having the formula, $-(CHR^3)m-$, in which
$R^3$ is H or $C_{1-4}$-alkyl and m=1 or 2;
X is $C_{2-6}$ alkylene or phenylene;
$R^1$ and $R^2$ each independently is H or alkyl or together, with X and the N atoms to which they are attached, represent a diazaheterocycle;
R is a substituted triazinylaminophenyl species of the formula,

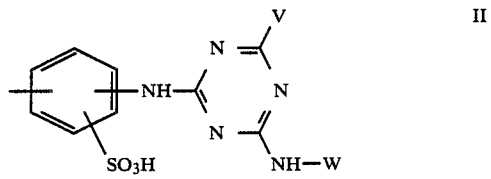

wherein W represents phenyl substituted by sulphonic or carboxylic acid groups and V represents $C_{1-4}$-alkoxy, amino, $C_{1-4}$-alkylamino or di($C_{1-4}$-alkyl)amino;
n is 0 or 1; and
Z is H or a group, $-Y-B$ being a heterocyclic cellulose-reactive group, selected from the group consisting of dichloropyrimidinyl, difluoropyrimidinyl, trichloropyrimidinyl, 5-chloridfluoropyrimidinyl, 5-cyanodichloropyrimidinyl, dichlorotriazinyl and monochlorotriazinyl.

3. A compound according to claim 2 wherein W is selected from 3-sulphophenyl, 2-sulphophenyl and 3-carboxyphenyl.

4. A compound according to claim 2 wherein $R^1$ and $R^2$ are each independently selected from H and $C_{1-4}$-alkyl.

5. A compound according to claim 2 wherein $Y-B$, is monochlorotriazinyl, carrying a phenyl group or a phenyl group substituted by a group selected from sulphonate, carboxylate, nitro, $C_{1-4}$-alkyl or alkoxy and halogen, such as chlorine and bromine.

6. A protein precipitant of the formula:

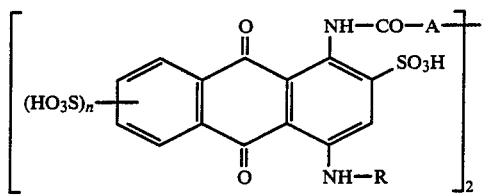
wherein A, X, R, $R^1$, $R^2$, Y and n are as defined in claim 1; & K is 0 or 1.
* * * * *